June 3, 1975 R. KORDES Plant Pat. 3,726
ROSE PLANT
Filed March 7, 1974
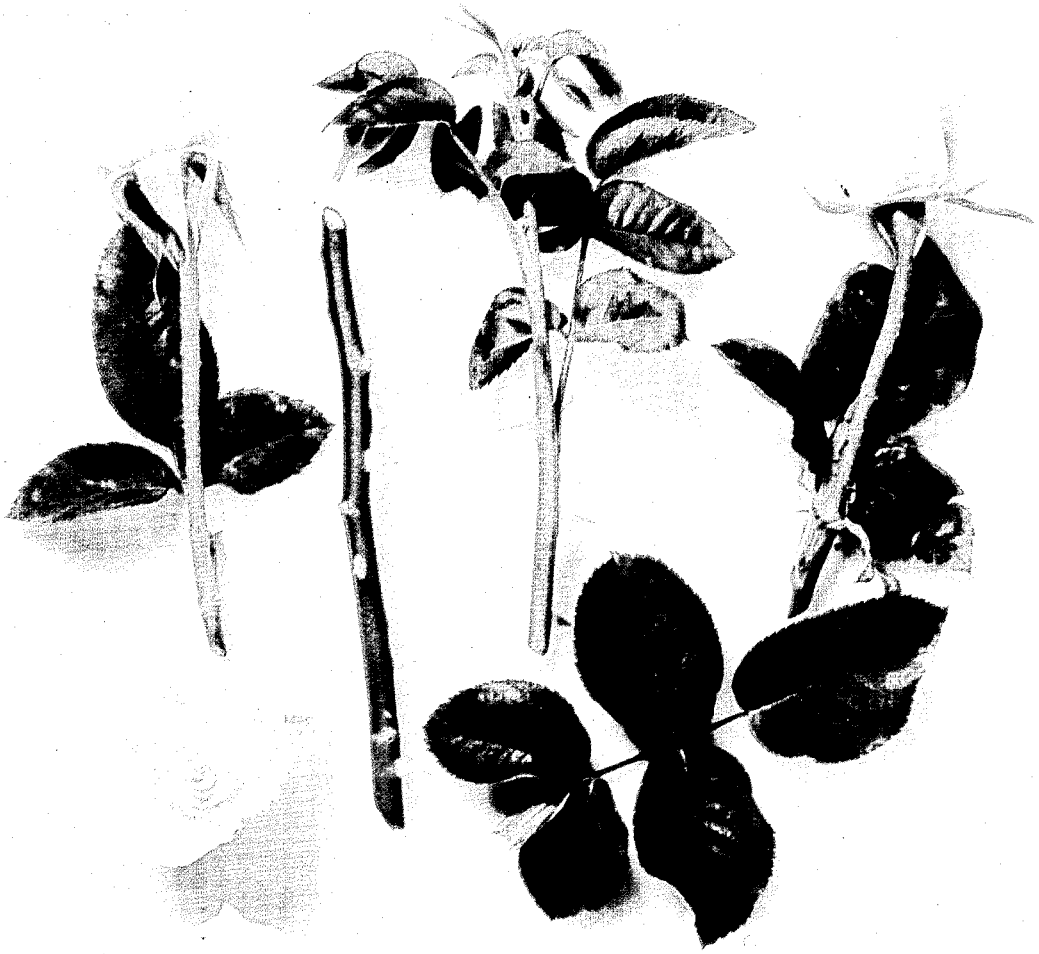

United States Patent

Plant Pat. 3,726

Patented June 3, 1975

3,726

ROSE PLANT

Reimer Kordes, Sparrieshoop, Germany, assignor to Jackson & Perkins Company, Medford, Oreg.

Filed Mar. 7, 1974, Ser. No. 449,070

Int. Cl. A01h *5/00*

U.S. Cl. Plt.—15 1 Claim

This present invention relates to a new and distinct cultivar of rose plant of the hybrid tea class which was originated by crossing an unnamed, undisseminated cultivar with pollen from the cultivar Peer Gynt.

The primary objective of this breeding was to produce a rose cultivar of the hybrid tea class, of a yellow color and which was suitable for use as a greenhouse grown cut flower cultivar. This objective was fully achieved as evidenced by the unique combination of characteristics which are outstanding in the new cultivar and which distinguish it from its parents as well as from all other cultivars of which I am aware.

1. A well branched habit of growth.
2. Stem lengths normally in the medium lengths.
3. Consistently, from season to season, a bud color of bright Lemon Yellow.
4. An abundance of large leathery leaves.
5. Very little fragrance.
6. Heavy petal substance.
7. A large, high centered open flower which lightens in color very little after opening.

Asexual reproduction of this new cultivar by budding, as performed at Sparrieshoop, Germany and Irvine, Calif., shows the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.
- *Seed parent.*—Unnamed seedling.
- *Pollen parent.*—Peer Gynt.

Classification:
- *Bontanical.*—Rosa hybrid.
- *Commercial.*—Hybrid tea.

FLOWER

Observations were made at Irvine, Calif., in mid-December 1973, from plants grown in greenhouse.

Blooming habit: Recurrent: continuous.

Bud:
- *Size.*—3.5 cm. when petals start to unfurl.
- *Form.*—Pointed, broad base.
- *Color.*—When sepals first divide, near Lemon Yellow 4 to 4/1 (Wilson). When half blown, upper side of petals, near Lemon Yellow 4/1 (Wilson). Lower side of petals, near Lemon Yellow 4/2 (Wilson).

Sepals:
- *Color.*—Outer surface—Scheeles Green 860/3 (Wilson). Inner surface—slightly deeper than Scheeles Green 860/3 (Wilson) covered with white tomentum. Three appendaged sepals lightly appendaged. Two unappendaged sepals, hairy edged.

Receptacle:
- *Color.*—Scheeles Green 860/3 (Wilson).
- *Shape.*—Funnel.
- *Size.*—Large, broad.
- *Surface.*—Smooth.

Peduncle:
- *Length.*—Medium short.
- *Surface.*—Prickly.
- *Color.*—Scheeles Green 860/3 (Wilson).
- *Strength.*—Stiff, erect, heavy.

Opening: Petals fold out—not in a spiral manner.

BLOOM

- *Size.*—Very large, average open size 11–12 cm.
- *Borne.*—Mostly singly.
- *Stems.*—Short, strong.
- *Form.*—When first open—high center. Permanence—retains its form to the end.
- *Petalage.*—Number of petals under normal conditions 30–35.
- *Color.*—Center of flower: upper side of petals, Chrome Yellow 605/1 (Wilson). Reverse side of petals—same. Base of petals—same. General tonality from a distance—Chrome Yellow 605/1 (Wilson). Variegations, occasional green streak on outer petals.
- *Discoloration.*—General tonality at end of first day—same—605/1 (Wilson). By third day—Chrome Yellow 605/2 (Wilson).
- *Fragrance.*—Slight.
- *Petals.*—Texture: thick. Shape: broadly oval. Form: edges slightly quilled. Arrangement: imbricated. Persistence: drop off cleanly. Lastingness—on the plant—long. As cut flower—long.

REPRODUCTIVE PARTS

- *Anthers.*—Medium, many. Color—Chinese Yellow 606 (Wilson). Arrangement—regular around styles.
- *Filaments.*—Color: Orange 12 (Wilson).
- *Pollen.*—Gold yellow.
- *Styles.*—Mostly white.
- *Stigmas.*—Yellow.

PLANT

- *Form.*—Bush.
- *Growth.*—Vigorous, upright, branching.

Foliage: Number of leaflets on normal mid-stem leaves—5.
- *Size.*—Large.
- *Quantity.*—Normal.
- *Color.*—New foliage: Scheeles Green 860/3 (Wilson) overlaid with a color lighter but of same hue as Garnet Brown 00918/3 (Wilson). Old foliage: near Spinach Green 0960 (Wilson).

Leaflets:
- *Shape.*—Oval.
- *Texture.*—Upper side—leathery.
- *Edge.*—Serrated.
- *Serration.*—Single, small.
- *Petiole.*—Rachis—color—mostly green. Underside—prickles.
- *Stipules.*—Long, slightly bearded.
- *Disease Resistance.*—Average resistance to mildew under normal growing conditions at Irvine, Calif.

Wood:
- *New wood.*—Color—light green.
- *Bark.*—Smooth.
- *Old wood.*—Color—green.
- *Bark.*—Smooth.

Prickles:
- *Quantity.*—On main stalks from base—ordinary. On laterals from stalk—ordinary.

*Form.*—Narrow base, long, hooked downward.
*Color when young.*—Green.
*Position.*—Irregular.

Small prickles:

*Quantity.*—Few on main stalks. Few on laterals.
*Color.*—Green.

I claim:

1. A new and distinct cultivar of rose plant of the hybrid tea class, substantially as herein shown and described, characterized particularly as to novelty by the unique combination of its pointed, broad based bud of bright Lemon Yellow; an abundance of large, leathery, non-glossy foliage; well branched habit of growth; medium stem length of its cut flowers; high centered imbricated form of blooms; a petal count of 30 to 35; and very little fragrance.

No references cited.

ROBERT E. BAGWILL, Primary Examiner